(12) United States Patent
Kiernan et al.

(10) Patent No.: US 8,739,796 B2
(45) Date of Patent: Jun. 3, 2014

(54) TRACHEAL TUBE FLANGE MEMBER

(75) Inventors: Declan Kiernan, Longford (IE); Kamlesh Sethiya, Athlone (IE); Mary Dempsey, Ballinasloe (IE)

(73) Assignee: Covidien LP, Mansfield, MA (US)

( * ) Notice: Subject to any disclaimer, the term of this patent is extended or adjusted under 35 U.S.C. 154(b) by 235 days.

(21) Appl. No.: 13/248,689

(22) Filed: Sep. 29, 2011

(65) Prior Publication Data

US 2013/0081634 A1  Apr. 4, 2013

(51) Int. Cl.
*A61M 16/04* (2006.01)

(52) U.S. Cl.
CPC .......... *A61M 16/0465* (2013.01); *A61M 16/04* (2013.01)
USPC .................. 128/207.14; 128/207.17

(58) Field of Classification Search
CPC ................ A61M 16/04; A61M 16/0465
USPC ............ 128/207.14–207.17; 602/42–59
See application file for complete search history.

(56) References Cited

U.S. PATENT DOCUMENTS

| 5,013,307 | A | 5/1991 | Broida |
| 5,058,579 | A | 10/1991 | Terry et al. |
| 5,203,806 | A | 4/1993 | Broida |
| 6,527,641 | B1 | 3/2003 | Sinclair et al. |
| 6,881,875 | B2 | 4/2005 | Swenson |
| 2003/0060247 | A1 | 3/2003 | Goldberg et al. |
| 2004/0229700 | A1 | 11/2004 | Cannon et al. |
| 2007/0167226 | A1 | 7/2007 | Kelly et al. |
| 2008/0072911 | A1 | 3/2008 | Flagler et al. |
| 2009/0126740 | A1 | 5/2009 | Loescher |
| 2009/0320852 | A1* | 12/2009 | Cuevas et al. ............ 128/207.14 |
| 2010/0089403 | A1* | 4/2010 | Solly ........................ 128/207.14 |
| 2010/0307488 | A1* | 12/2010 | Poulsen et al. .......... 128/200.26 |
| 2012/0048277 | A1* | 3/2012 | Waldron et al. ......... 128/207.14 |
| 2012/0130297 | A1* | 5/2012 | Loescher ........................ 602/54 |

OTHER PUBLICATIONS

Medical Dynamics, Inc.—Technology of the Future, Today; B & B Medical Technologies; B&B Deny Ties; http://www.thinkmdi.net/html/BB.php; May 26, 2011.

* cited by examiner

*Primary Examiner* — Justine Yu
*Assistant Examiner* — Valerie L Skorupa
(74) *Attorney, Agent, or Firm* — Fletcher Yoder PC

(57) ABSTRACT

Various embodiments of flange members and tracheostomy tube assemblies including such flange members are provided. An embodiment of a flange member includes a base portion adapted to receive a proximal end of a cannula, a first flange disposed on a first side of the base portion, and a second flange member disposed on a second side of the base portion opposite the first side. The first flange and the second flange are adapted to rest against a patient's neck to maintain the flange member outside of a patient's airway. The flange member also includes a biocompatible pad reversibly integrated with at least one of the base portion, the first flange, and the second flange.

20 Claims, 3 Drawing Sheets

TRACHEAL TUBE FLANGE MEMBER

BACKGROUND

The present disclosure relates generally to medical devices and, more particularly, to airway devices, such as tracheostomy tubes.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices, such as tracheal tubes, may be used to control the flow of air and medicaments into or out of a patient's airway. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

More specifically, tracheal tubes may be used to control the flow of air or other gases through a patient's trachea. Such tracheal tubes may include endotracheal tubes or tracheostomy tubes. While patients may be intubated using endotracheal tubes during emergencies or shorter hospital stays, tracheostomy tubes are typically used for prolonged ventilation, as the use of a tracheostomy tube may be more comfortable for a patient.

A typical tracheostomy tube is generally inserted into the trachea via a stoma, which is a surgical incision in the neck. After insertion of the tube into the trachea, a portion of the tracheostomy tube remains outside the patient. This portion extends outwards from the neck and may connect the tracheostomy tube to a ventilator or other medical device. Generally, this exterior portion of the tube is held in place by a flange that rests on the patient's neck and is further secured by straps to the patient. The inserted portion of the tracheostomy tube is generally mechanically coupled to the flange, typically by a snap or screw mechanism or bonding on the underside of the flange, which rests on the patient's neck. During prolonged intubation periods, this mechanical connection point may cause irritation at the stoma site, thereby causing discomfort for the patient. Additionally, the portions of the flange that contact the patient's neck are often rigid, and, accordingly, when such portions rub against the patient's neck during movement of the patient, the patient may experience additional discomfort.

Certain devices attempt to address these problems by providing pillow or fabric protectors for the neck that may lift the flange slightly off the neck to avoid skin irritation, providing some additional comfort. However, these devices may be a less stable base for the tube at the patient's neck. Additionally, these devices often need to be replaced during periods of prolonged intubation, and it can be difficult for a medical practitioner to replace these devices since they are typically located between the flange and the patient's neck. Accordingly, there exists a need for tracheostomy tubes that overcome these drawbacks.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
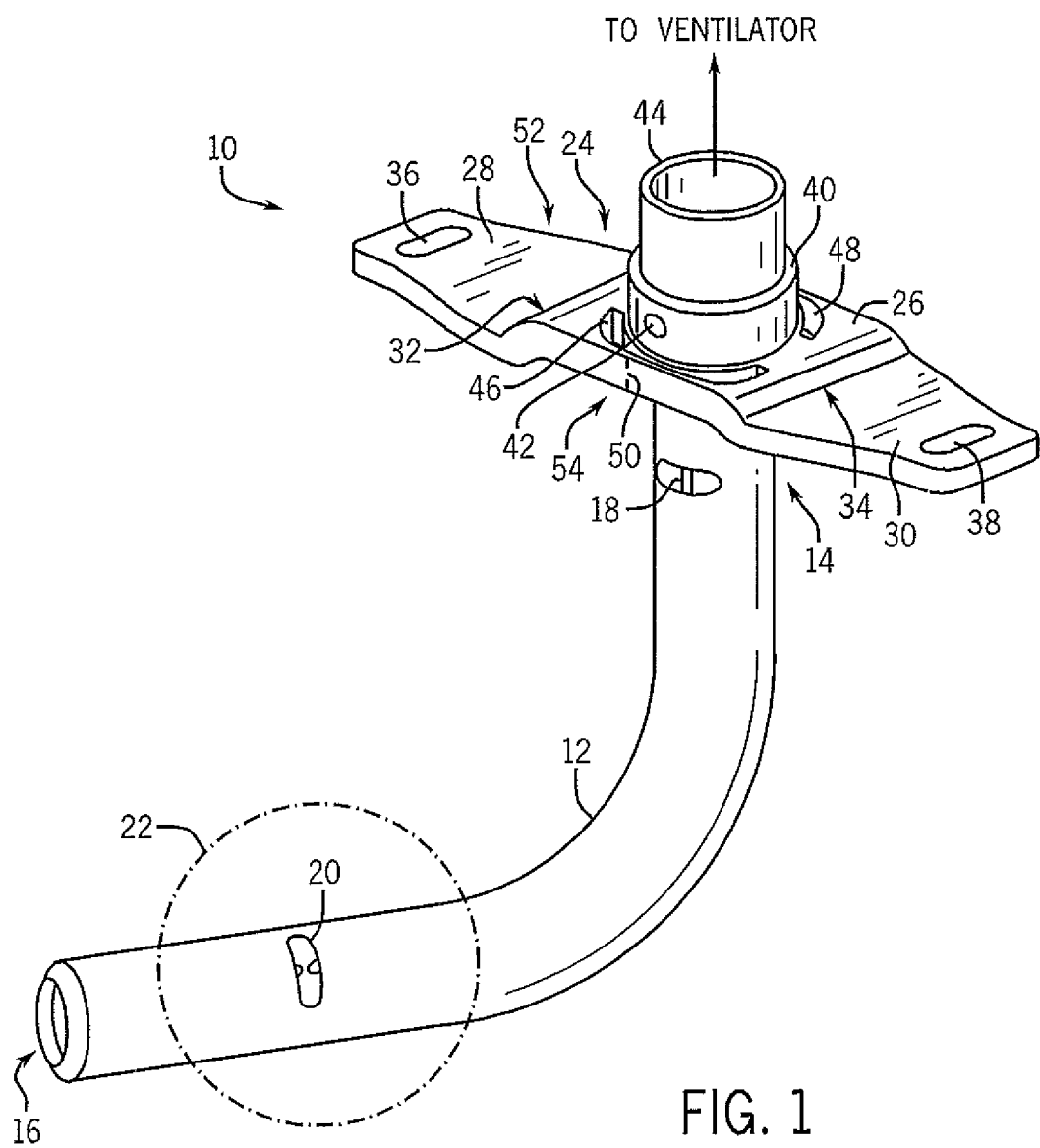
FIG. 1 is a perspective view of a tracheostomy tube including a flange member having a biocompatible pad integrated therein in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, provided herein are tracheostomy tube assemblies including a flange member having an integral pad capable of reducing or eliminating discomfort at the stoma site of a patient. In presently contemplated embodiments, the pad may be formed from a biocompatible material having suitable mechanical, biological, and chemical properties. For example, the pad may be partially or completely formed from an antimicrobial compound, a biocompatible polymer, a gelatinous material, or a combination thereof. Still further, the pad may have one or more features that enable the removal and replacement of the pad from the flange member, for example, to replace the pad during periods of prolonged ventilation. Furthermore, in some embodiments, one or more apertures may also be disposed in the flange member to enable airflow to the stoma site, which may reduce patient discomfort since the presence of air at the stoma site may aid in patient healing.

The provided tracheostomy tube assemblies may be disposable rather than reusable and may be capable of conveying gas to and from the patient, such as during medical situations that necessitate prolonged ventilation. As such, the devices and techniques provided herein may enable maintaining a bidirectional gas flow between the patient and an external ventilation device. Accordingly, the tracheostomy tube assemblies provided herein may be adapted to be inserted into the trachea via a surgical incision in the neck such that after insertion of the tube into the trachea, a portion of the tube remains outside the patient. This portion extends outwards from the neck and may connect the tracheostomy tube to a ventilator or other medical device. That is, the provided tracheostomy tube assemblies may be used in conjunction with auxiliary devices, such as airway accessories, ventilators, humidifiers, and so forth, which may cooperate with the tube assemblies to maintain airflow to and from the lungs of the patient. For example, the tracheal tubes may be coupled to an adapter or connector that is configured to couple the tracheostomy tube assemblies described herein to the desired auxiliary device.

Turning now to the drawings, FIG. 1 is a perspective view of an exemplary tracheostomy tube assembly 10. In the depicted embodiment, the tracheostomy tube assembly 10 includes an arcuate cannula 12 having a proximal end 14 and a distal end 16, which is generally sized and configured to be inserted into a patient's neck through a surgical incision for prolonged ventilation. When the tracheostomy tube assembly 10 is in use, the distal end 16 as well as the major portion of the length of the cannula 12 will reside within the trachea, with the proximal end 14 being generally flush with the anterior surface of the patient's neck. The cannula 12 may also feature a lumen 18 within the wall, terminating in notch 20 that may be used to fill a balloon type sealing cuff 22 at the patient insertion end. In some embodiments, the cuff 22 may be a urethane balloon bonded to the exterior of the cannula 12 such that the notch 20 is encompassed. In certain embodiments, the cuff 22 may be inflated within the patient's airway, for example, via lumen 18 to provide an additional seal. However, in other embodiments, the cannula 12 may be provided without the cuff 22.

The cannula 12 and the cuff 22 may be formed from materials having desirable mechanical properties (e.g., puncture resistance, pin hole resistance, tensile strength, and so forth) and desirable chemical properties (e.g., biocompatibility). In one embodiment, the walls of the cuff 22 may be made of a polyurethane (e.g., Dow Pellethane® 2363-80A) having suitable mechanical and chemical properties. In other embodiments, the walls of the cuff 22 may be made of a suitable polyvinyl chloride (PVC). In certain embodiments, the cuff 22 may be generally sized and shaped as a high volume, low pressure cuff that may be designed to be inflated to pressures between about 15 cm and 30 cm of water. Furthermore, the cuff 22 may be any of a variety of suitable cuffs, such as a tapered cuff or a non-tapered cuff.

In some embodiments, the cannula 12 may also include a suction lumen (not shown in FIG. 1) that extends from a location on the proximal end 14 of the cannula 12 positioned outside the body when in use to a location around the cuff 22 inside the body. The suction lumen may terminate in a port through which secretions accumulated around the cuff may be aspirated. For example, a port may be located above the cuff 22 or one or more ports may be located anywhere along the length of the cannula 12 such that they aspirate secretions from the airway of the patient. Further, in some embodiments, an exterior suction tube may connect to the suction lumen for the removal of the suctioned fluids, for example, via a vacuum connected to the exterior suction tube.

The tracheostomy tube assembly 10 also features a flange member 24 connected to the proximal end 14 of the cannula 12. When the distal end 16 of the cannula 12 is placed within the patient's airway, the flange member 24 is designed to rest on the neck of the patient to maintain a portion of the tracheostomy tube assembly 10 outside of the patient's body. To that end, in the depicted embodiment, the flange member 24 includes a base portion 26 flanked by a first flange 28 and a second flange 30. The first flange 28 and the second flange 30 are coupled to the base portion 26 via a first stepped portion 32 and a second stepped portion 34, respectively. The flanges 28 and 30 of the flange member 24 may include features that enable the flange member 24 to securely rest on the neck of a patient during use. For example, the flanges 28 and 30 may feature openings 36 and 38 designed to accommodate attachment straps that may secure the tracheostomy tube assembly 10 to the neck.

Further, the flange 24 may include an extension 40 extending from the base portion 26 and having an aperture 42 that may facilitate the attachment of the flange member 24 to the proximal end 14 of the cannula 12. The illustrated flange member 24 also features a conduit 44 that is substantially in-line with the proximal end 14 of the cannula 12. Generally, the conduit 44 may be adapted to connect the tracheostomy tube assembly 10 to any suitable medical device. For example, the conduit 44 may serve as an insertion point for a disposable cannula lining, for example, in double cannula tracheostomy tubes including an inner and outer cannula, or may be suitably sized and shaped to connect the tracheostomy tube assembly 10 via medical tubing or other devices to a mechanical ventilator.

In certain embodiments, the flange member 24 may include features that enable air to reach a stoma site of a patient when the distal end 16 of the cannula 12 is positioned within the patient's airway. For example, in the illustrated embodiment, the base portion 26 of the flange member 24 includes a first aperture 46 and a second aperture 48 that each extend through the thickness 50 of the base portion 26 to enable airflow from a first side 52 of the flange member 24 to a second side 54 of the flange member 24. The foregoing feature may be advantageous because air may more easily reach the healing stoma site in presently contemplated designs, which may result in less irritation experienced by the patient at the stoma site.

Figure 2:
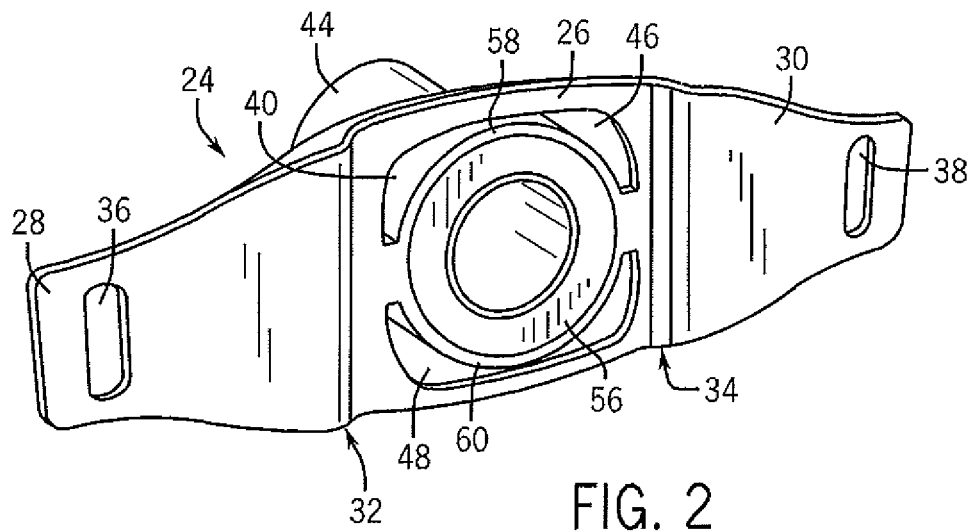
FIG. 2 is a bottom perspective view of the flange member of FIG. 1 illustrating the biocompatible pad disposed therein in accordance with an embodiment.
Figure 3:
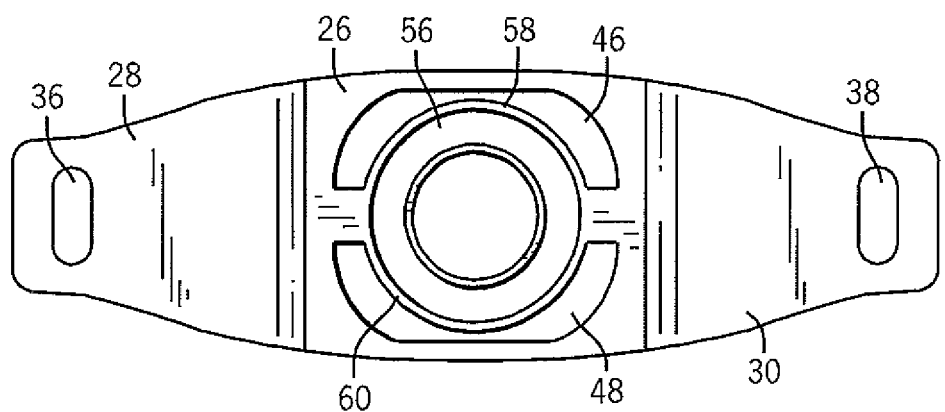
FIG. 3 is a bottom view of the flange member of FIG. 1 illustrating apertures disposed about the biocompatible pad in accordance with an embodiment.

Furthermore, the flange member 24 may also include a pad 56 integrated with the base portion 26 of the flange member 24, as illustrated in more detail in FIGS. 2 and 3. More specifically, as shown, the pad 56 is a circular pad integrated between semicircular portions 58 and 60 of the base portion 26. In the depicted embodiment, the apertures 40 and 48 are semicircular apertures disposed about the semicircular portions 58 and 60 to enable airflow to the area surrounding the pad 56, thereby reducing the likelihood of patient discomfort at the stoma site.

In presently contemplated embodiments, the pad 56 may be formed from materials having desirable mechanical properties (e.g., puncture resistance, tensile strength, etc.), desirable chemical properties (e.g., biocompatibility), and desirable biological properties (e.g., antimicrobial). For example, in one embodiment, the pad 56 may be made of a biocompatible polymer capable of promoting healing at the stoma site, for example, in the presence of air. Further, in certain embodiments, the pad 56 may be gelatinous and may be designed to deliver one or more healing promoters to the stoma site, or the pad 56 may be substantially dry prior to placement in the flange member 24. In general, where desired, the pad 56 may comprise or be designed to hold any solid or liquid phase agent that resists infection and/or irritation, and/or that promotes healing of the tissue at and/or around the stoma site.

In the illustrated embodiment, the pad 56 is circular in shape and is surrounded by semicircular apertures 46 and 48. However, the illustrated shapes are merely examples, and the size and shape of the pad 56 and apertures 46 and 48 are subject to considerable implementation-specific variations in other embodiments. For example, in another embodiment, the pad 56 may be substantially rectangular in shape to follow the general shape of base portion 26. Additionally, the location of the integrated pad 56 in the flange member 24 may also vary in different implementations. For example, in other embodiments, one or more pads 56 may be provided in the base portion 26, the first flange 28, the second flange 30, or a combination thereof.

As illustrated in FIGS. 2 and 3, the pad 56 may be integrated with the flange member 24 during portions of the usage period of the flange member 24. The foregoing feature may offer advantages over traditional flanges, which may be utilized with a stoma pad that is generally placed between the flange and the patient's neck. For example, the integration of the pad 56 in the flange member 24 may provide a more stable attachment of the flange member 24 to the patient's neck, thereby decreasing patient discomfort. Furthermore, in embodiments in which the pad 56 includes one or more components or layers capable of promoting healing at the stoma site, patient discomfort may be further reduced as compared to traditional designs.

Figure 4:
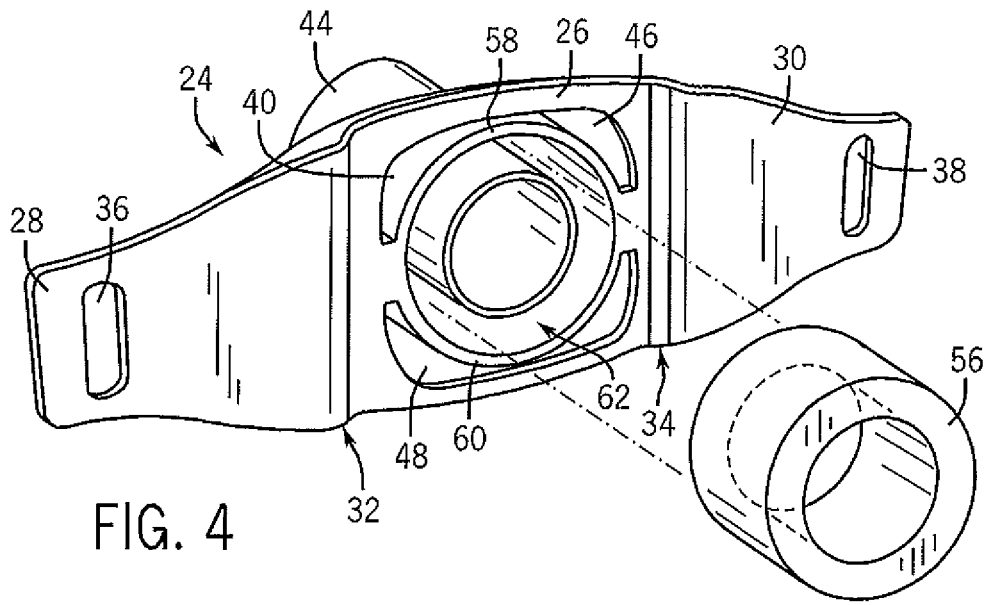
FIG. 4 is an exploded bottom perspective view of the flange member of FIG. 1 illustrating the biocompatible pad removed from a recess in accordance with an embodiment.

Features of the illustrated flange member 24 that may enable integration of the pad 56 into the flange member 24 are shown in more detail in the exploded perspective view of FIG. 4. As shown, the base portion 26 of the flange member 24 includes a recess 62 suitably sized and shaped to receive the pad 56. When coupled together, the pad 56 may be retained in the recess 62 in a reversible engagement. For example, in certain embodiments, the pad 56 may be retained in the recess 62 during usage periods through a friction fit, inclusion of an adhesive material on the pad 56, or in any other suitable way. In certain embodiments, the positioning of the pad 56 in the recess 62 may be reversible by an operator without the use of tools. That is, the operator may use personally generate force to remove the pad 56 from the recess. In such embodiments, the pad 56 may include one or more features (e.g., a slit) that facilitate such removal, as discussed in more detail below. Still further, in other embodiments, the engagement between the pad 56 and the recess 62 may require the use of a handheld tool to reverse the engagement and remove the pad 56, for example, for replacement during periods of prolonged ventilation.

It should be noted that the recess 62 may be susceptible to various implementation-specific variations in other embodiments. For example, the shape and size of the recess 62 may be altered to accommodate pads 56 of various shapes and sizes. Further, the recess 62 may include one or more retaining members capable of facilitating the retainment of the pad 56 in the recess 62. For example, the retaining members may include notches or bars capable of securing the pad 56 in the recess 62 when suitably positioned within or around the recess 62.

Figure 5:
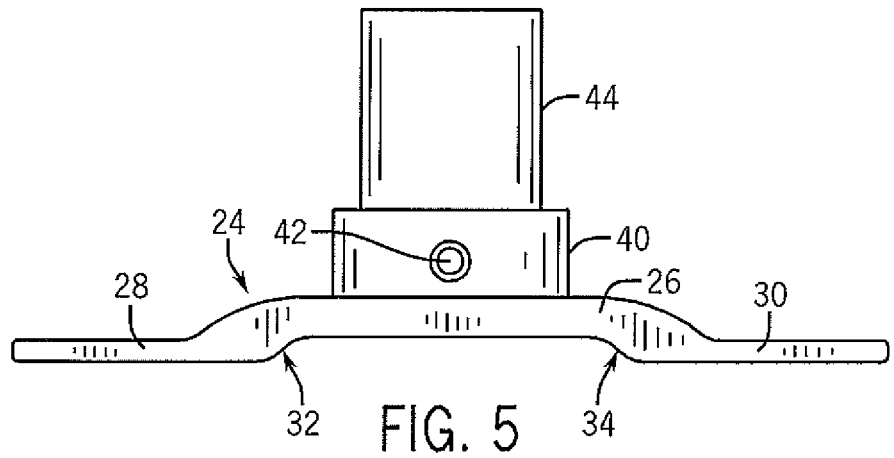
FIG. 5 is a front view of the flange member of FIG. 1 in accordance with an embodiment.

FIG. 5 is a front view of the flange member 24 illustrating features of the flange member 24 in more detail. As shown, the stepped portions 32 and 34 couple the first flange 28 and the second flange 30 to the base portion 26. During operation, when the flange member 24 is positioned against the patient's neck, the flanges 28 and 30 rest against the patient's neck to maintain a portion of the tracheostomy tube assembly 10 outside of the patient's trachea. In the illustrated embodiment, however, the base portion 26 of the flange member 24 is maintained at a distance from the patient's neck because of the stepped portions 32 and 34. However, in other embodiments, the portions 32 and 34 may not be stepped, and the base portion 26 may rest against the patient's neck as well. Still further, although not illustrated in FIG. 5, in some embodiments, the pad 56 may extend outward from the base portion 26 such that the pad 56 is adapted to engage with the patient's neck.

Figure 6:
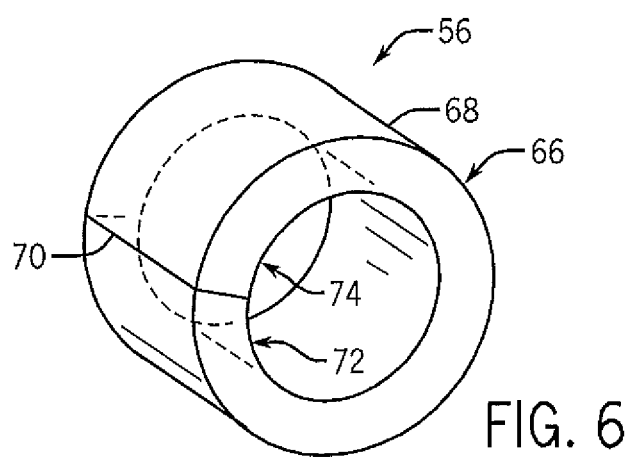
FIG. 6 is a perspective view of a biocompatible pad having a slit in accordance with an embodiment.

FIG. 6 is a perspective view illustrating an embodiment of the pad 56 in more detail. In this embodiment, the pad 56 is formed as an annular ring 66 having an annular wall 68. The annular wall 68 includes a slit 70 capable of facilitating removal of the pad 56 from the recess 62 of the flange member 24. For example, an operator may utilize the slit 70 to separate a first portion 72 of the annular wall 68 from a second portion 74 of the annular wall 68 to enable removal of the pad 56 from the recess 62, for example, for replacement of the pad 56. It should be noted that the slit 70 may be susceptible to variations in dimensions and shape depending on the given application, or the slit 70 may not be provided in some embodiments.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheostomy tube assembly, comprising:
   a cannula comprising a distal end and a proximal end, the distal end being configured to be inserted into a patient's trachea;
   a flange member disposed about the proximal end of the cannula and configured to support the tracheostomy tube assembly via engagement with a patient's neck to maintain the flange member outside of the patient's trachea, wherein the flange member comprises a recess formed as a continuous annular ring; and
   a pad formed as an annular ring, wherein at least a portion of the pad is configured to be received in the continuous annular recess of the flange member to couple the pad to the flange member such that a ring-shaped surface of the pad abuts the patient's neck when the flange member supports the tracheostomy tube assembly via engagement with the patient's neck.

2. The tracheostomy tube assembly of claim 1, comprising a conduit disposed on the proximal end of the cannula and being configured to operatively connect to a medical device.

3. The tracheostomy tube assembly of claim 2, wherein the medical device comprises an airway accessory, a ventilator, a humidifier, or a combination thereof.

4. The tracheostomy tube assembly of claim 1, wherein the pad comprises an antimicrobial compound, a biocompatible polymer, a gelatinous material, an adhesive material, or a combination thereof.

5. The tracheostomy tube assembly of claim 1, wherein the flange member comprises at least one aperture proximal to the continuous annular recess and configured to enable airflow to a stoma site of the patient.

6. The tracheostomy tube assembly of claim 1, wherein the flange member comprises a central portion configured to receive the proximal end of the cannula and a first flange and a second flange disposed on opposite sides of the central portion, and wherein a first stepped portion and a second stepped portion couple the first flange and the second flange, respectively, to the central portion, and wherein the pad is configured to extend outward from the central portion to engage with the patient's neck.

7. The tracheostomy tube assembly of claim 1, wherein the flange member comprises a base portion configured to receive the proximal end of the cannula and a first flange and a second flange disposed on opposite sides of the base portion, and wherein the pad and the base portion are configured to rest against the patient's neck.

8. The tracheostomy tube assembly of claim 1, comprising a cuff disposed about the distal end of the cannula and configured to be inflated to seal against walls of the patient's trachea.

9. The tracheostomy tube assembly of claim 1, wherein the flange member comprises a pair of apertures configured to receive securement straps adapted to secure the tracheostomy tube assembly to the patient's neck.

10. A flange member for an airway device, the flange member comprising:
   a base portion comprising a central aperture configured to receive a proximal end of a cannula and a continuous annular recess disposed about the central aperture;
   a first flange disposed on a first side of the base portion;
   a second flange disposed on a second side of the base portion opposite the first side, wherein the first flange and the second flange are configured to rest against a patient's neck to maintain the flange member outside of a patient's airway; and
   an annular biocompatible pad, wherein the annular biocompatible pad is configured to be received in the continuous annular recess of the base portion and to abut the patient's neck when the first flange and the second flange rest against the patient's neck.

11. The flange member of claim 10, wherein the annular biocompatible pad comprises an antimicrobial compound, a biocompatible polymer, a gelatinous material, an adhesive material, or a combination thereof.

12. The flange member of claim 10, wherein the annular biocompatible pad is configured to extend outward from the base portion to engage with the patient's neck.

13. The flange member of claim 10, wherein the annular biocompatible pad comprises a slit configured to facilitate removal of the annular biocompatible pad from at least one of the base portion, the first flange, and the second flange.

14. The flange member of claim 10, comprising one or more apertures disposed in at least one of the base portion, the first flange, and the second flange in a position proximate to the annular biocompatible pad and configured to facilitate airflow to a stoma site of a patient.

15. The flange member of claim 10, wherein the first flange and the second flange each comprises an aperture configured to receive securement straps adapted to secure the flange member to the patient's neck.

16. A flange member for an airway device, the flange member comprising:
   a base portion comprising a central aperture configured to receive a proximal end of a cannula and a continuous annular recess disposed about the central aperture and configured to receive a biocompatible pad formed as an annular ring;
   a first flange disposed on a first side of the base portion;
   a second flange disposed on a second side of the base portion opposite the first side, wherein the first flange and the second flange are configured to rest against a patient's neck to maintain the flange member outside of a patient's airway; and
   one or more apertures disposed in at least one of the base portion, the first flange, and the second flange, and being configured to enable airflow to a stoma site of a patient.

17. The flange member of claim 16, wherein a first stepped portion and a second stepped portion couple the first flange and the second flange, respectively, to the base portion.

18. The flange member of claim 17, wherein the biocompatible pad is configured to extend outward from the base portion to engage with the patient's neck when the first flange and the second flange rest against the patient's neck.

19. The flange member of claim 16, wherein the one or more apertures comprises two apertures disposed in the base portion about the continuous annular recess.

20. The flange member of claim 19, wherein the two apertures are semicircular apertures disposed about the circumference of the continuous annular recess.

* * * * *